United States Patent
Silver

(10) Patent No.: US 9,326,744 B2
(45) Date of Patent: *May 3, 2016

(54) MONOCHROMATIC X-RAY METHODS AND APPARATUS

(71) Applicant: Eric H. Silver, Needham, MA (US)

(72) Inventor: Eric H. Silver, Needham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/752,804

(22) Filed: Jun. 26, 2015

(65) Prior Publication Data

US 2015/0366526 A1    Dec. 24, 2015

Related U.S. Application Data

(63) Continuation of application No. 14/475,432, filed on Sep. 2, 2014, now Pat. No. 9,066,702, which is a continuation of application No. 13/709,597, filed on Dec. 10, 2012, now abandoned, which is a (Continued)

(51) Int. Cl.
*G01N 23/04* (2006.01)
*A61B 6/00* (2006.01)
(Continued)

(52) U.S. Cl.
CPC .............. *A61B 6/485* (2013.01); *A61B 6/022* (2013.01); *A61B 6/4035* (2013.01);
(Continued)

(58) Field of Classification Search
CPC ...... A61B 6/482; A61B 6/485; A61B 6/4064; A61B 6/4035; A61B 6/503; A61B 6/5288; A61B 6/022; A61B 6/5264; G01N 23/04; A61N 5/10; A61N 2005/1091
See application file for complete search history.

(56) References Cited

U.S. PATENT DOCUMENTS 3,801,785 A    4/1974 Barrett
3,867,637 A    2/1975 Braun et al.
(Continued)

FOREIGN PATENT DOCUMENTS

DE    19639243 A1    4/1998
JP    H01-190337 A    7/1989
(Continued)

OTHER PUBLICATIONS

Kuramoto et al., Sharpening of an energy band of diagnostic x-ray spectrum with metal filters. World Congress Medical Physics and Biomedical Engineering. 2006;3(3):1533-1536.

(Continued)

*Primary Examiner* — Courtney Thomas
(74) *Attorney, Agent, or Firm* — Wolf, Greenfield & Sacks, P.C.

(57) ABSTRACT

According to some aspects, an x-ray apparatus for imaging and/or radiation therapy is provided, the x-ray apparatus comprises an electron source capable of generating electrons, at least one first target arranged to receive electrons from the electron source, the at least one first target comprising material that, in response to being irradiated by the electrons, emits broad spectrum x-ray radiation, at least one second target arranged to receive at least some of the broad spectrum x-ray radiation, the at least one second target comprising material that, in response to irradiation by broad spectrum x-ray radiation from the first target, emits monochromatic x-ray radiation, and at least one detector positioned to detect at least some of the monochromatic x-ray radiation emitted from the at least one second target. According to some aspects, a relatively low cost, relatively small footprint x-ray apparatus for generating monochromatic x-ray radiation suitable for medical/clinical purposes and appropriate for use in existing medical facilities such as hospitals and/or small clinical settings is provided.

20 Claims, 14 Drawing Sheets

Related U.S. Application Data continuation of application No. 12/761,724, filed on Apr. 16, 2010, now Pat. No. 8,331,534.

(60) Provisional application No. 61/169,969, filed on Apr. 16, 2009.

(51) Int. Cl.
*H05G 2/00* (2006.01)
*A61B 6/02* (2006.01)
*A61N 5/10* (2006.01)

(52) U.S. Cl.
CPC .............. *A61B 6/4064* (2013.01); *A61B 6/482* (2013.01); *A61B 6/50* (2013.01); *A61B 6/503* (2013.01); *A61B 6/5276* (2013.01); *A61B 6/5288* (2013.01); *H05G 2/00* (2013.01); *A61B 6/5264* (2013.01); *A61N 5/10* (2013.01); *A61N 2005/1091* (2013.01); *A61N 2005/1098* (2013.01)

(56) References Cited

U.S. PATENT DOCUMENTS

| | | | |
|---|---|---|---|
| 4,048,496 | A | 9/1977 | Albert |
| 4,903,287 | A | 2/1990 | Harding |
| 4,945,552 | A | 7/1990 | Ueda et al. |
| 5,157,704 | A | 10/1992 | Harding |
| 5,787,146 | A | 7/1998 | Giebler |
| 5,940,469 | A | 8/1999 | Hell et al. |
| 6,141,400 | A | 10/2000 | Schardt et al. |
| 7,394,890 | B1 | 7/2008 | Wang et al. |
| 7,486,984 | B2 | 2/2009 | Carroll |
| 7,567,650 | B2 | 7/2009 | Harding et al. |
| 7,809,113 | B2 | 10/2010 | Aoki et al. |
| 8,331,534 | B2 | 12/2012 | Silver |
| 9,066,702 | B2 * | 6/2015 | Silver .................. A61B 6/4035 |
| 2006/0153332 | A1 | 7/2006 | Kohno et al. |
| 2006/0176997 | A1 | 8/2006 | Dilmanian et al. |
| 2013/0188773 | A1 | 7/2013 | Silver et al. |

FOREIGN PATENT DOCUMENTS

| | | |
|---|---|---|
| JP | 06-109898 A | 4/1994 |
| JP | 06-277205 A | 10/1994 |
| JP | 07-095044 A | 4/1995 |
| JP | 2001-008924 A | 1/2001 |
| JP | 2002-521676 A | 7/2002 |
| JP | 2005-237730 A | 9/2005 |
| JP | 2008-016339 A | 1/2008 |
| WO | WO 00/05727 A1 | 2/2000 |
| WO | WO 2008/052002 A2 | 5/2008 |

OTHER PUBLICATIONS

Silver et al., The x-ray: reloaded. RT-IMAGE. Dec. 2008;1:21(48).
Extended European Search Report mailed Nov. 19, 2013 for Application No. 10764778.6.
International Search Report and Written Opinion mailed Dec. 7, 2010 for International Application No. PCT/US2010/001142.

* cited by examiner

MONOCHROMATIC X-RAY METHODS AND APPARATUS

RELATED APPLICATIONS

This Application claims the benefit under 35 U.S.C. §120 and is a continuation of U.S. application Ser. No. 14/475,432, entitled "MONOCHROMATIC X-RAY METHODS AND APPARATUS" filed on Sep. 2, 2014, which claims the benefit under 35 U.S.C. §120 and is a continuation of Ser. No. 13/709,597, entitled "MONOCHROMATIC X-RAY METHODS AND APPARATUS" filed on Dec. 10, 2012, which claims the benefit under 35 U.S.C. §120 and is a continuation of U.S. application Ser. No. 12/761,724, entitled "MONOCHROMATIC X-RAY METHODS AND APPARATUS" filed on Apr. 16, 2010, which claims priority under 35 U.S.C. §119(e) to U.S. Provisional Application Ser. No. 61/169,969, entitled "A LOW COST, TABLE-TOP, MONOCHROMATIC X-RAY DIAGNOSTIC AND THERAPEUTIC SYSTEM" filed on Apr. 16, 2009, each of which are herein incorporated by reference in their entirety.

BACKGROUND

Traditional diagnostic radiography and cancer therapy use X-ray generators that emit X-rays over a broad energy band which unnecessarily exposes normal tissue during diagnosis and treatment. Monochromatic radiation has been used in specialized settings in attempts to reduce the dose and improve image contrast. However, conventional systems for generating monochromatic radiation may be unsuitable for clinical or commercial use due to prohibitive size, cost and/or complexity. For example, utilizing an inefficient Bragg crystal as a filter or using a solid target x-ray fluorescer to generate monochromatic radiation requires a very large, expensive and powerful broad band synchrotron source, which has not proven practical for clinical settings.

Other conventional techniques include using polycapillary optics to increase the throughput from conventional laboratory X-ray generators, but Bragg crystals are still used to monochromatize. In some therapeutic applications, high energy linear electron accelerators are used to reduce the dose to the skin. However, control over energy specificity is indirect and minimal. It is typically impossible to target a specific type or depth of tissue using a single radiation beam and the radiation is indiscriminant of tissue types, whether malignant or benign. Further, the cost, infrastructure, and personnel requirements of today's treatment facilities is high and it is unlikely to meet even a fraction of society's healthcare needs. Brachytherapy using monochromatic Gamma-ray sources may offer therapeutic benefits as well, but the appropriate choices of radionuclides are limited because Gamma-ray energies and half-lives are fixed by the natural laws of physics.

SUMMARY

Applicant has appreciated that a standard x-ray tube for generating broad spectrum radiation may be combined with a fluorescent target to generate monochromatic radiation suitable for imaging target tissue and for radiation therapy. Aspects of the invention may be utilized to provide a relatively low cost, relatively small footprint x-ray apparatus for generating monochromatic x-ray radiation suitable for medical/clinical purposes and appropriate for use in existing medical facilities such as hospitals.

Some embodiments include a method of generating monochromatic radiation comprising generating broad spectrum x-ray radiation from an x-ray tube comprising a first target that, in response to being irradiated by electrons, emits the broad spectrum x-ray radiation, directing at least some of the broad spectrum x-ray radiation to irradiate a second target comprising material that, in response to the irradiation, emits monochromatic x-ray radiation, and directing at least some of the monochromatic x-ray radiation to irradiate the target tissue.

Some embodiments include an x-ray apparatus comprising an electron source capable of generating electrons, at least one first target arranged to receive electrons from the electron source, the at least one first target comprising material that, in response to being irradiated by the electrons, emits broad spectrum x-ray radiation, at least one second target arranged to receive at least some of the broad spectrum x-ray radiation, the at least one second target comprising material that, in response to irradiation by broad spectrum x-ray radiation from the first target, and at least one detector positioned to detect at least some of the monochromatic x-ray radiation emitted from the at least one second target.

DETAILED DESCRIPTION

Figure 1:
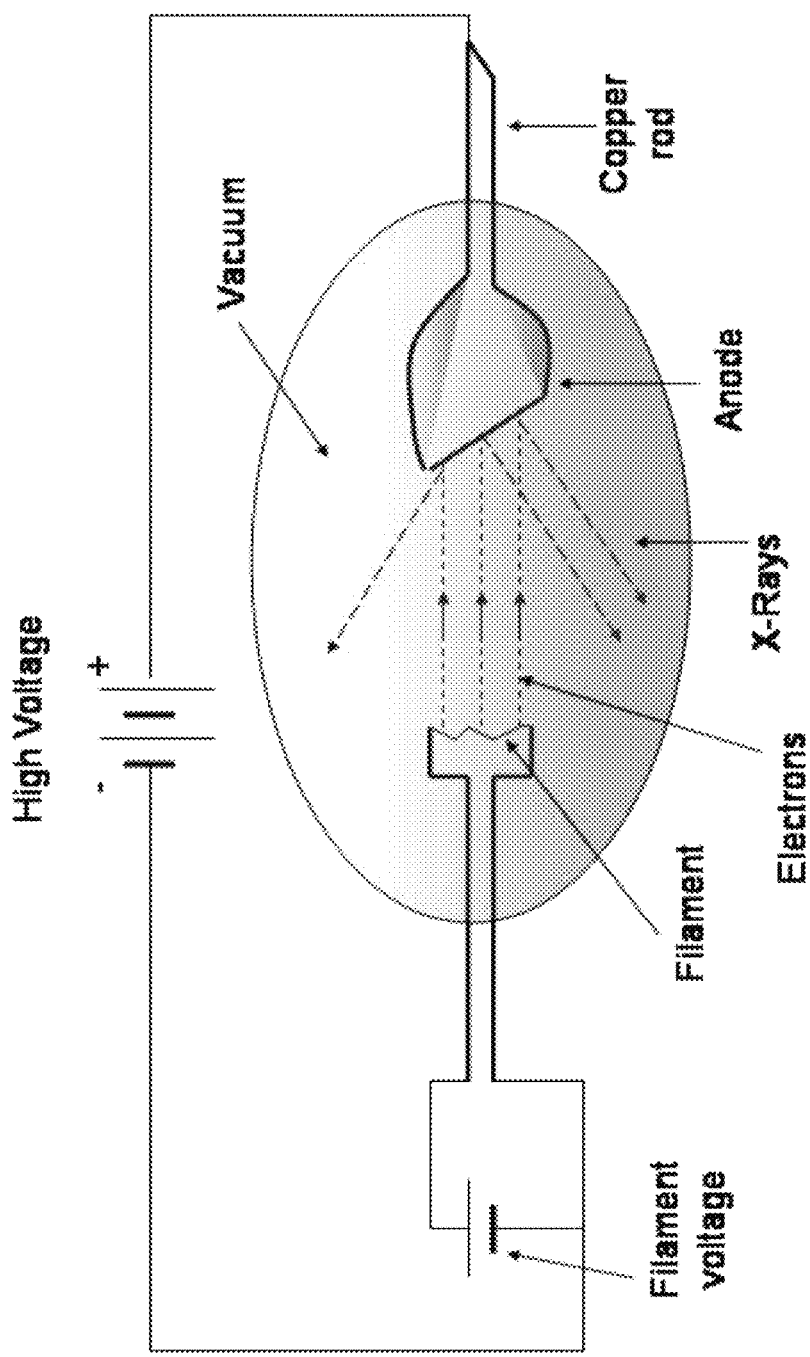
FIG. 1 is a schematic of a conventional X-ray tube.

As discussed above, conventional x-ray systems capable of generating monochromatic radiation to produce diagnostic images and/or perform radiation therapy are typically not suitable for clinical and/or commercial use due to the prohibitively high costs of manufacturing, operating and maintaining such systems and/or system footprints that are much too large for clinical use. As a result, such conventional systems are limited in application to investigation at and by the relatively few research institutions that have invested in large, complex and expensive equipment. Medical facilities such as hospitals and clinics remain without a viable option for monochromatic x-ray equipment that can be adopted in a clinical setting for diagnostic/therapeutic purposes.

Applicant has developed a simple, low-cost, table-top method and apparatus for producing tunable monochromatic x-radiation capable of efficiently diagnosing and treating cancerous tumors. According to some embodiments, a conventional x-ray tube that generates x-rays over a broad energy range is used to irradiate a solid target, which in turn, will emit monochromatic fluorescent x-rays. The fluorescing target may be made from a single element or it may be a composite of several elements. The energies of these fluorescent x-rays are characteristic of the elemental composition of the target material. A target made from a single element may be selected so that the energy of its fluorescent x-rays just exceeds the absorption edge of the dominant element in a contrast agent that has been delivered to specific tissue sites such as cancerous tumors.

In this sense, the fluorescent x-ray emission from the target is tuned to the absorption characteristics of the contrast agent. That is, the fluorescent target includes material that matches the contrast agent. The contrast agent may be any suitable contrast agent such as any one or combination of bromine, iodine, gadolinium, silver, gold, platinum, other elements with an atomic number greater than 35, or any other suitable contrast agent. The contrast agent may belong to at least one of the class of contrast agents such as x-ray imaging agents, magnetic resonance imaging agents, radioactive agents, radiation therapy agents, thyroid-related agents, antiseptics, disinfectants, expectorants, anti-amoebics, anti-virals, anti-arrhythmic, anti-neo-plastics, etc.

Such techniques enhance x-ray absorption in the contrast agent relative to the surrounding tissue, thereby not only improving image contrast but lowering diagnostic radiation doses as much as three orders of magnitude. According to some embodiments, a multi-element target may be chosen that will emit fluorescent X-rays with energies that are below and above the absorption edge of the contrast agent. The difference in absorption obtained simultaneously above and below the edge can further improve the image contrast. By increasing the power of the conventional x-ray tube for therapeutic applications, the targeting capability techniques described herein increase absorption efficiency at tumor sites, or wherever the contrast agent is located, while minimizing radiation exposure elsewhere.

According to some embodiments, a monochromatic x-ray device is provided by, at least in part, combining in series a target that produces broad spectrum radiation in response to an incident electron beam, followed by a fluorescing target that produces monochromatic x-ray in response to incident broad spectrum radiation. The term "broad spectrum radiation" is used herein to describe Bremsstralung radiation with or without characteristic emission lines of the anode material. The principle of operation of such a device is described in further detail below.

Thick Target Bremsstrahlung

Figure 2:
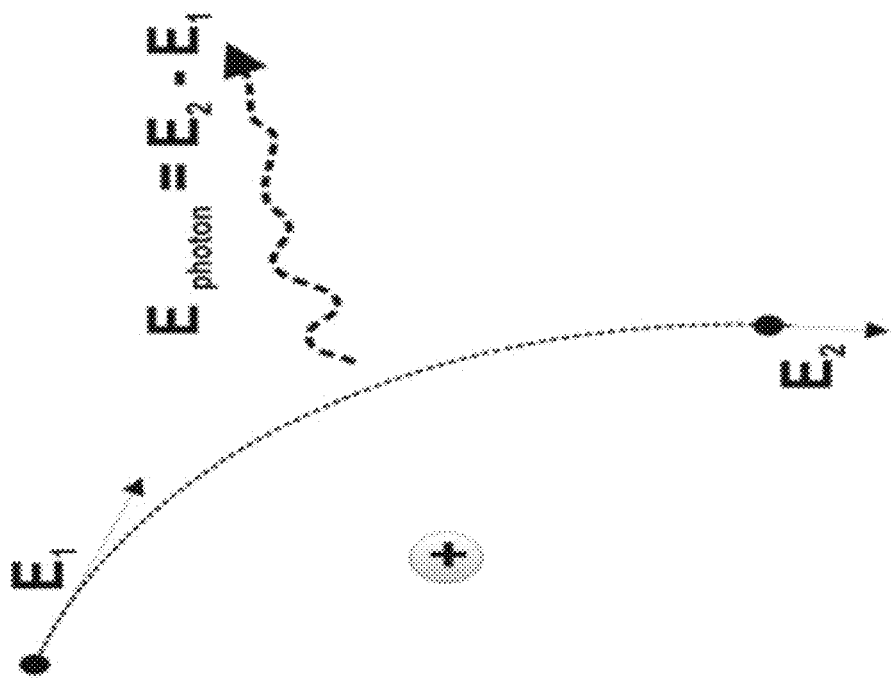
FIG. 2. illustrates the scenario in which an electron (much lighter than the nucleus) comes very close to the nucleus and the electromagnetic interaction causes a deviation of the trajectory where the electron loses energy and an X-ray photon is emitted and describes Bremsstralung in its simplest form.

In an X-ray tube electrons are liberated from a heated filament called the cathode and accelerated by a high voltage (e.g., ~50 kV) toward a metal target called the anode as illustrated schematically in FIG. 1. The high energy electrons interact with the atoms in the anode. Often an electron with energy $E_1$ comes close to a nucleus in the target and its trajectory is altered by the electromagnetic interaction. In this deflection process, it decelerates toward the nucleus. As it slows to an energy $E_2$, it emits an X-ray photon with energy $E_2-E_1$. This radiation is called Bremsstrahlung radiation (braking radiation) and the kinematics are shown in FIG. 2

Figure 3:
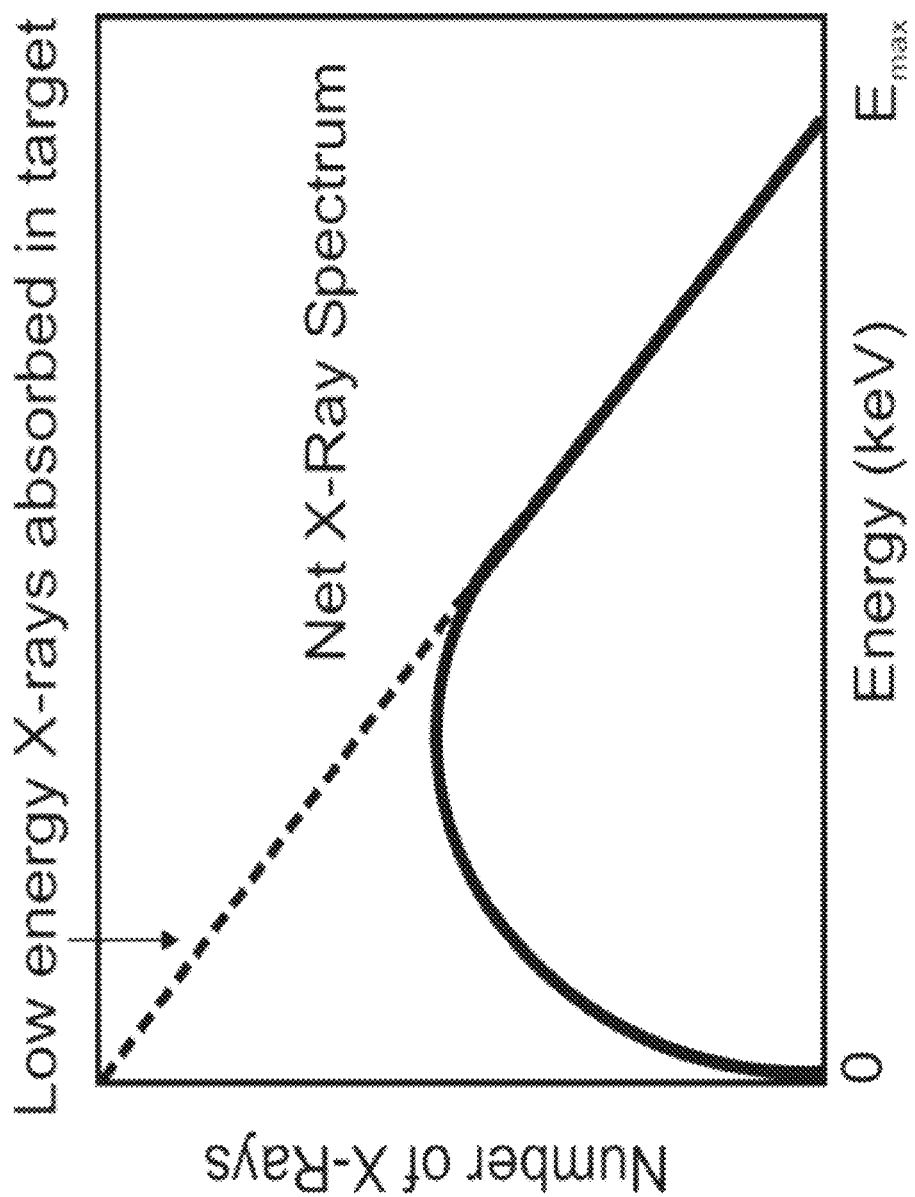
FIG. 3 illustrates the Bremsstrahlung spectrum produced by a typical X-ray tube, wherein the lower energy x-rays trying to escape the target are absorbed causing the characteristic roll over of the spectrum at low energies.

The energy of the emitted photon can take any value up to the maximum energy of the incident electron, $E_{max}$. As the electron is not destroyed it can undergo multiple interactions until it loses all of its energy or combines with an atom in the anode. Initial interactions will vary from minor to major energy changes depending on the actual angle and proximity to the nucleus. As a result, Bremsstrahlung radiation will have a generally continuous spectrum, as shown in FIG. 3. The probability of Bremsstrahlung production is proportional to $Z^2$, where Z is the atomic number of the target material, and the efficiency of production is proportional to Z and the x-ray tube voltage. Note that low energy Bremsstrahlung X-rays are absorbed by the thick target anode as they try to escape from deep inside causing the intensity curve to bend over at the lowest energies, as discussed in further detail below.

Characteristic Line Emission

Figure 4:
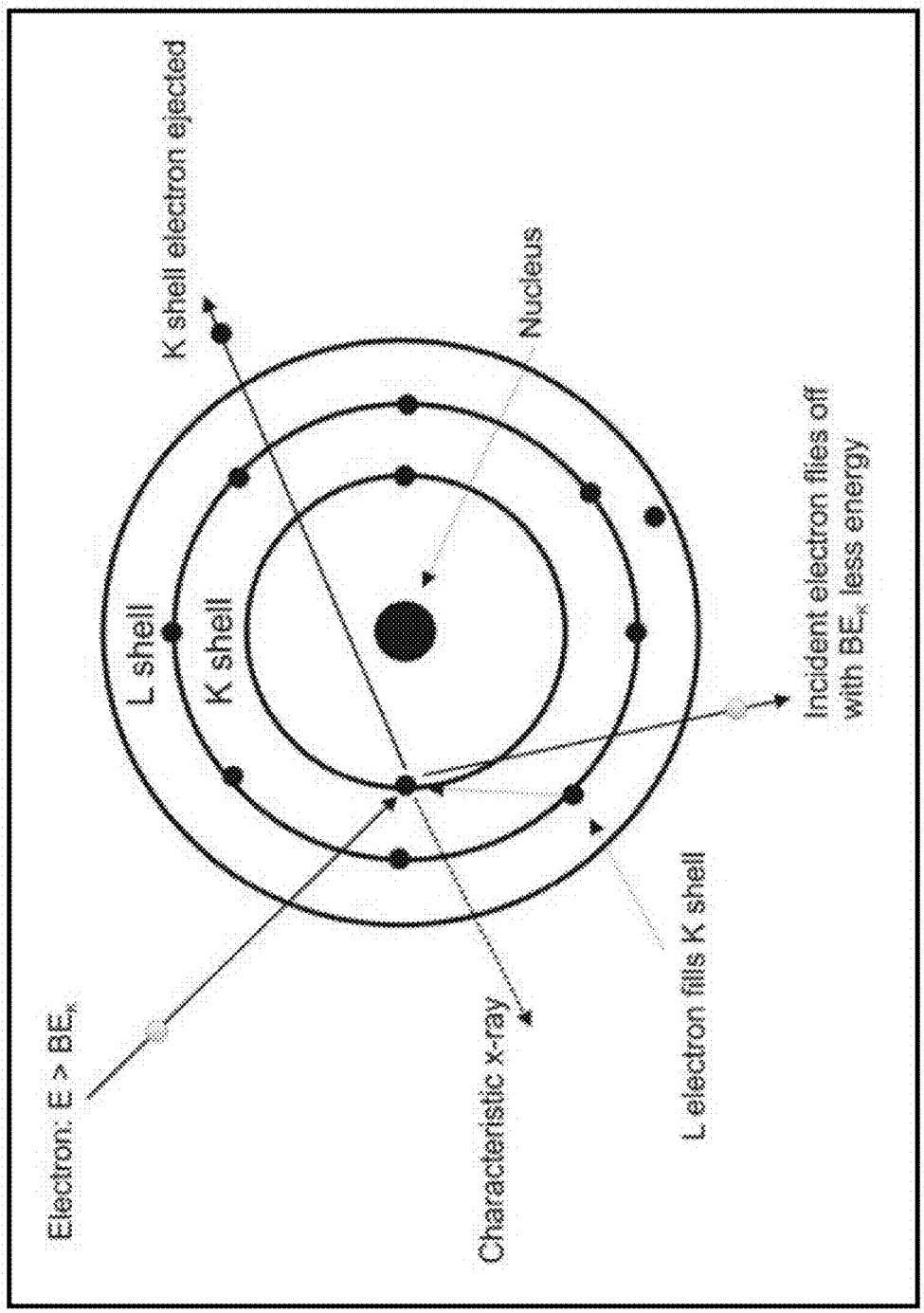
FIG. 4 illustrates the physical phenomenon that generates characteristic line emissions.
Figure 5:
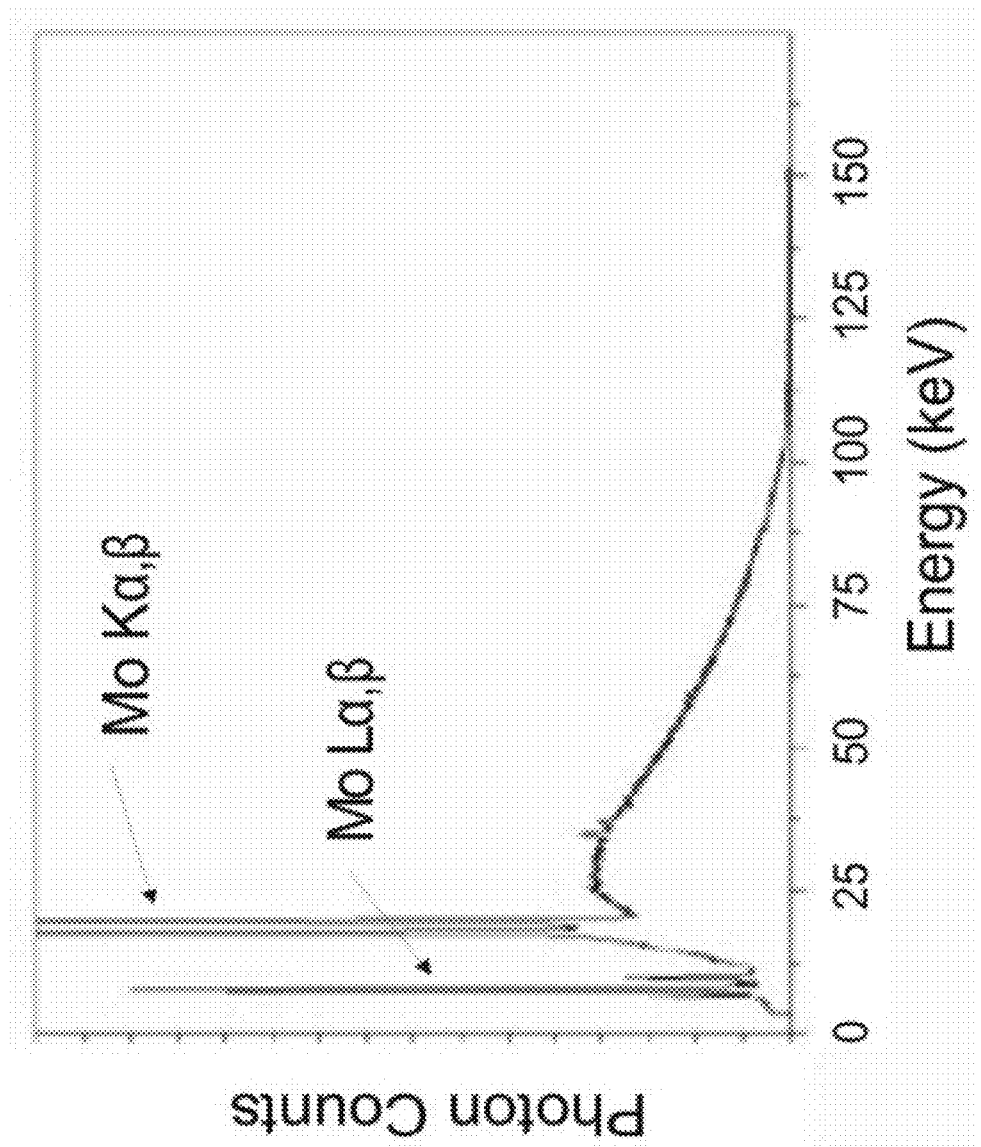
FIG. 5 illustrates the combined spectrum from an X-ray tube with a molybdenum anode showing the thick target Bremsstrahlung and the characteristic molybdenum line emission.

While most of the electrons slow down and have their trajectories changed, some will collide with electrons that are bound by an energy, BE, in their respective orbitals or shells that surround the nucleus in the target atom. As shown in FIG. 4, these shells are denoted by K, L, M, N, etc. In the collision between the incoming electron and the bound electron, the bound electron will be ejected from the atom if the energy of the incoming electron is greater than BE of the orbiting electron. For example, the impacting electron with energy $E > BE_K$, shown in FIG. 4, will eject the K-shell electron leaving a vacancy in the K shell. The resulting excited and ionized atom will de-excite as an electron in an outer orbit will fill the vacancy. During the de-excitation, an X-ray is emitted with an energy equal to the difference between the initial and final energy levels of the electron involved with the de-excitation. Since the energy levels of the orbital shells are unique to each element on the Periodic Chart, the energy of the X-ray identifies the element. The energy will be monoenergetic and the spectrum appears monochromatic rather than a broad continuous band. Here, monochromatic means that the width in energy of the emission line is equal to the natural line width associated with the atomic transition involved. For copper Kα x-rays, the natural line width is about 4 eV. For Zr Kα, Mo Kα and Pt Kα, the line widths are approximately, 5.7 eV, 6.8 eV and 60 eV, respectively. The complete spectrum from an X-ray tube with a molybdenum target as the anode is shown in FIG. 5. The characteristic emission lines unique to the atomic energy levels of molybdenum are shown superimposed on the thick target Bremsstrahlung.

X-Ray Absorption and X-Ray Fluorescence

Figure 6A:
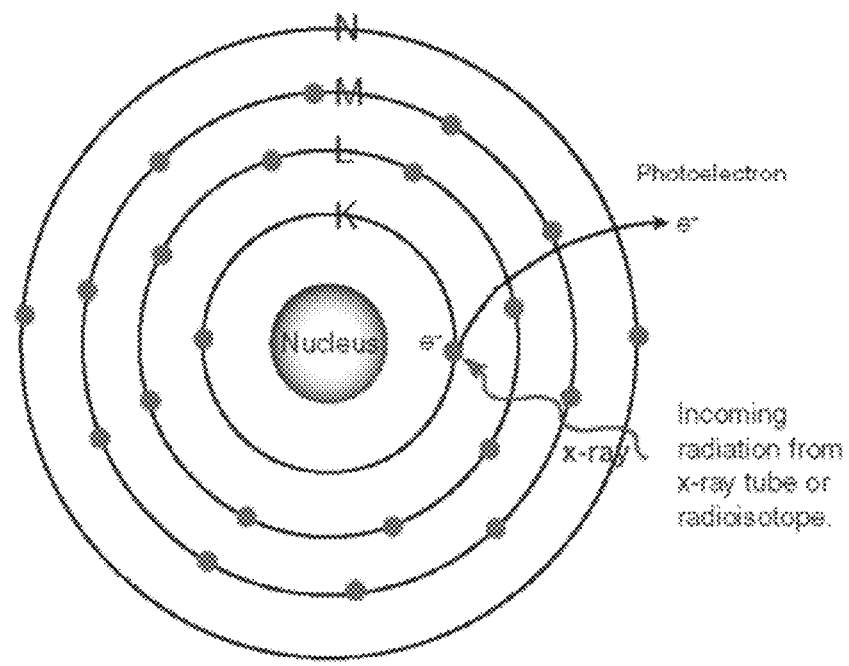
FIG. 6A illustrates the photoelectric effect.

When an x-ray from an x-ray tube strikes a sample, the x-ray can either be absorbed by an atom or scattered through the material. The process in which an x-ray is absorbed by an atom by transferring all of its energy to an innermost electron is called the photoelectric effect, as illustrated in FIG. 6A. This occurs when the incident x-ray has more energy than the binding energy of the orbital electron it encounters in a collision. In the interaction the photon ceases to exist imparting all of its energy to the orbital electron. Most of the x-ray energy is required to overcome the binding energy of the orbital electron and the remainder is imparted to the electron upon its ejection leaving a vacancy in the shell. The ejected free electron is called a photoelectron. A photoelectric interaction is most likely to occur when the energy of the incident photon exceeds but is relatively close to the binding energy of the electron it strikes. As an example, a photoelectric interaction is more likely to occur for a K-shell electron with a binding energy of 23.2 keV when the incident photon is 25 keV than if it were 50 keV. This is because the photoelectric effect is inversely proportional to approximately the third power of the X-ray energy.

Figure 6B:
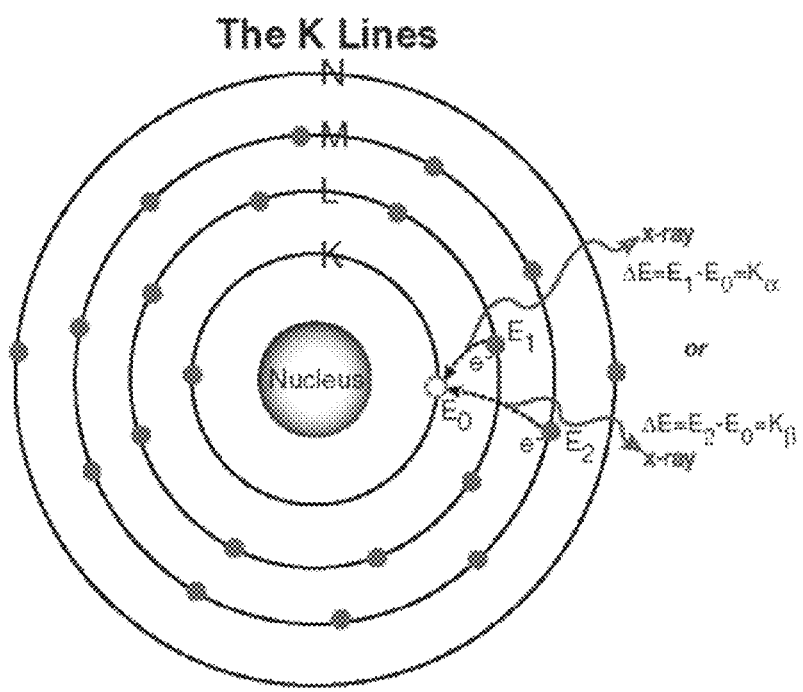
FIG. 6B illustrates the principle of X-Ray fluorescence from the K shell.
Figure 7:
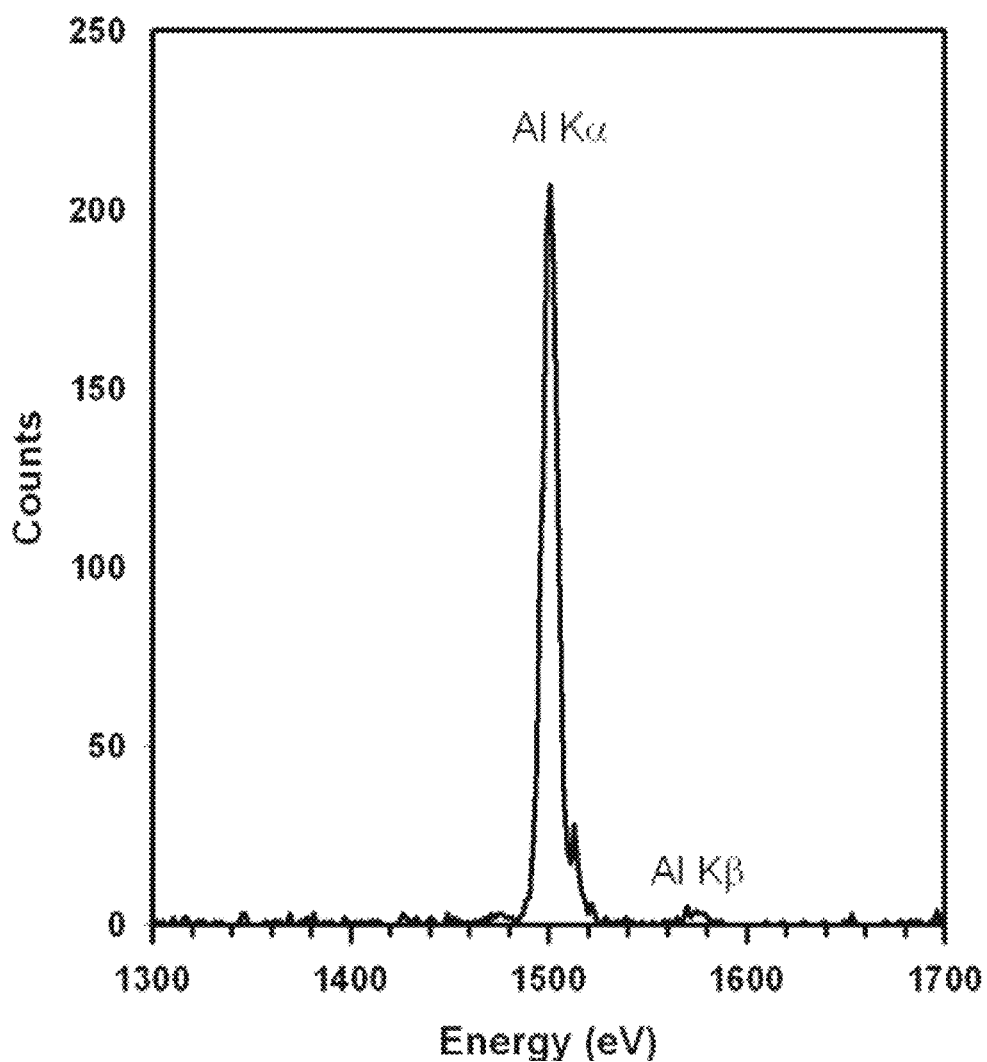
FIG. 7 illustrates an X-Ray fluorescence spectrum made by irradiating a target of aluminum (Al) with copper x-rays which were generated by an x-ray tube with an anode of copper.

The vacancies in the inner shell of the atom present an unstable condition for the atom. As the atom returns to its stable condition, electrons from the outer shells are transferred to the inner shells and in the process emit a characteristic x-ray whose energy is the difference between the two binding energies of the corresponding shells as described above in the section of Characteristic Line Emission. This photon-induced process of x-ray emission is called X-ray Fluorescence, or XRF. FIG. 6B shows schematically X-ray fluorescence from the K shell and a typical x-ray fluorescence spectrum from a sample of aluminum is shown in FIG. 7. The characteristic X-rays are labeled with a K to denote the shell where the original vacancy originated. In addition, alpha ($\alpha$) and beta ($\beta$) are used to identify the x-rays that originated from the transitions of electrons from higher shells. Hence, a K$\alpha$ x-ray is produced from a transition of an electron from the L to the K shell, and a K$\beta$ x-ray is produced from a transition of an electron from the M to a K shell, etc. It is important to note that these monoenergetic emission lines do not sit on top of a background of broad band continuous radiation; rather, the spectrum is Bremsstrahlung free. As discussed above, the x-ray tube produces thick target Bremsstrahlung and characteristic x-rays from the copper in the anode target. But when the combined spectral emission from the x-ray tube is used to irradiate the aluminum sample, only the monoenergetic emission lines, Al K$\alpha$ and Al K$\beta$ are produced via X-ray fluorescence.

Figure 8:
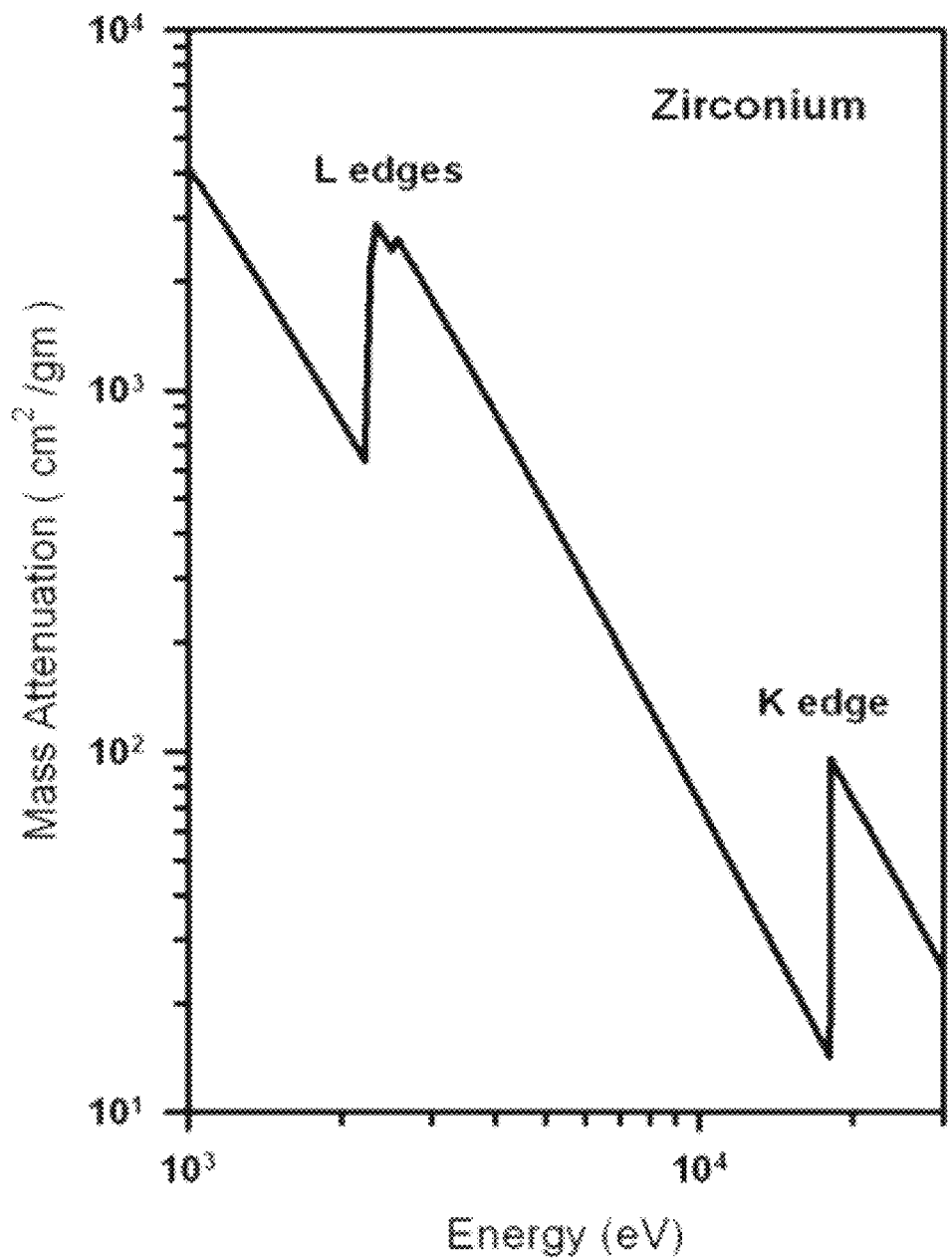
FIG. 8 illustrates the absorption coefficient as a function of x-ray energy for zirconium, wherein the discontinuous jumps or edges show how the absorption is enhanced just above the binding energies of the electrons in zirconium.

As mentioned above, the probability for x-ray absorption for a given absorbing element decreases with increasing energy of the incident photon. However, this fall-off is interrupted by a sharp rise when the x-ray energy is equal to the binding energy of an electron shell (K, L, M, etc.) in the absorber. This is the lowest energy at which a vacancy can be created in the particular shell and is referred to as the edge. FIG. 8 shows the absorption of Zirconium as a function of x-ray energy. The absorption is defined on the ordinate axis by its mass attenuation coefficient. The absorption edges corresponding to the binding energies of the L orbitals and the K orbitals are shown by the discontinuous jumps at approximately 2.3 keV and 18 keV, respectively. Every element on the Periodic Chart has a similar curve describing its absorption as a function of x-ray energy.

Following below are more detailed descriptions of various concepts related to, and embodiments of, methods and apparatus according to the present invention. It should be appreciated that various aspects of the invention described herein may be implemented in any of numerous ways. Examples of specific implementations are provided herein for illustrative purposes only. In addition, the various aspects of the invention described in the embodiments below may be used alone or in any combination, and are not limited to the combinations explicitly described herein.

Figure 9:
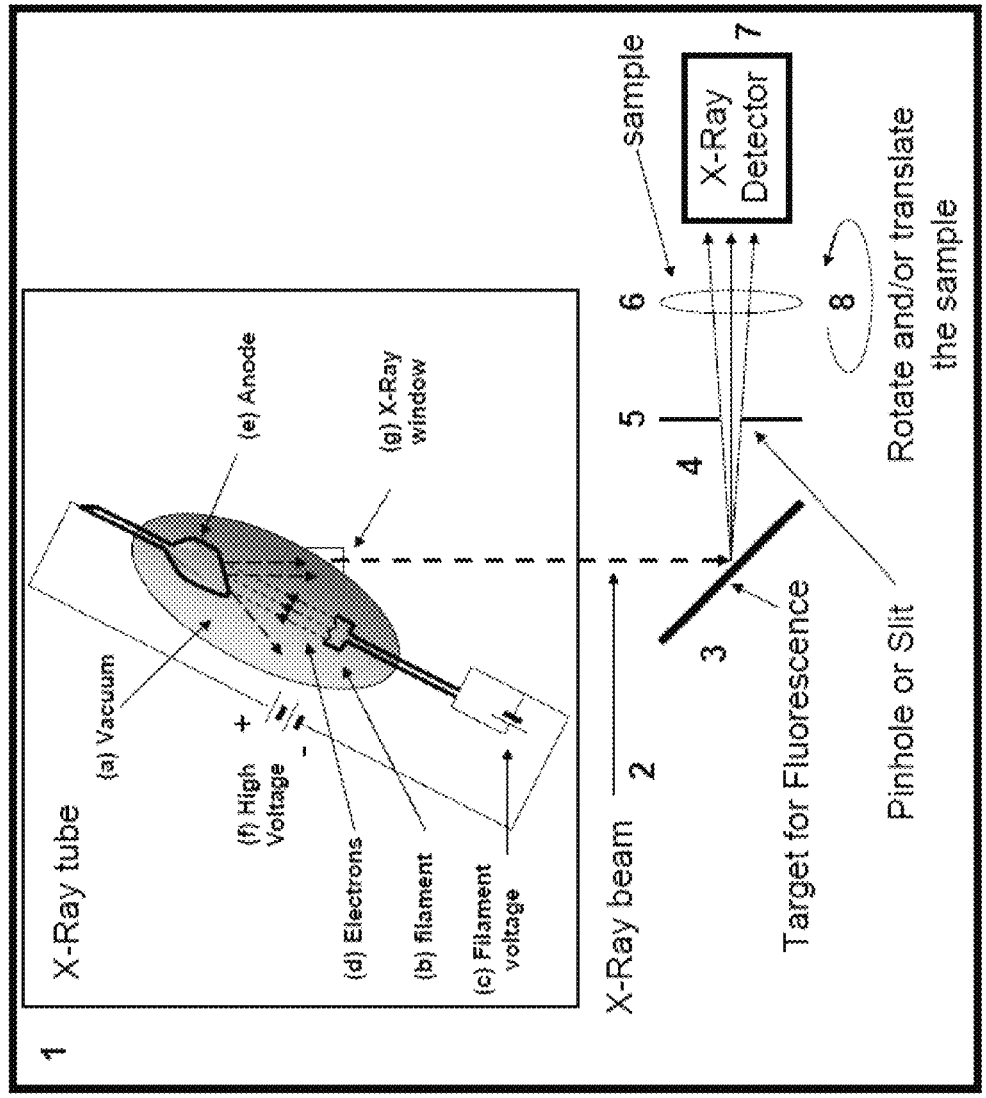
FIG. 9 illustrates a monochromatic x-ray system, in accordance with some embodiments of the present invention.

FIG. 9 illustrates a schematic of an x-ray apparatus for generating monochromatic x-rays, in accordance with some embodiments of the present invention. An x-ray tube 1 generates thick target Bremsstrahlung radiation by ohmically heating a filament (b) (which operates as the cathode) with a voltage (c) (typically 5-6 volts) so that the filament emits electrons (d). The electrons are accelerated toward the anode (e) due to the high voltage bias (f) of the anode with respect to the filament (which is typically at zero or ground potential). As the electrons are decelerated by the anode, they generate Bremsstrahlung radiation as shown in FIG. 3 and a significant amount of ohmic power is dissipated by the anode in the form of heat. This heat may be conducted from the anode material to the outside of the vacuum enclosure. Characteristic emission lines unique to the anode material may also be produced by the electron bombardment of the anode material provided the voltage potential is large enough. The x-ray radiation exits the vacuum enclosure through a window (g) that is vacuum tight so that the x-rays may be transmitted with high efficiency (e.g. beryllium).

It should be appreciated that x-ray tube 1 may be a standard x-ray tube for generating broad spectrum radiation. For example, the x-ray tube may be similar to or the same as conventional x-ray tubes currently being used in medical applications. Accordingly, some embodiments of the x-ray apparatus described herein are capable of being manufactured as a relatively low cost, table top solution. As a result, such x-ray apparatus may be suitable for widespread adoption by medical facilities such as hospitals to perform monochromatic x-ray diagnostic and/or therapeutic applications, as described in further detail below.

The x-ray beam 2 emitted from the x-ray tube irradiates a fluorescent target 3 which produces monochromatic x-radiation characteristic of the element(s) in the target in response to the x-rays incident on the target. The monochromatic x-rays 4 diverge through collimator (e.g., a pinhole or slit 5) and pass through the sample 6 (e.g., target tissue to be imaged or treated, as discussed in further detail below). Other components may be used to collimate the x-rays to form a pencil beam, a fan beam or any other shaped beam, as the aspects of the invention are not limited in this respect. The x-ray tube, fluorescent target and collimator are collectively referred to herein as the monochromatic x-ray source. The transmitted x-rays are detected by an x-ray detector 7 to produce an image of the sample.

For example, the monochromatic x-rays may penetrate a 2D cross-section of the sample to ultimately produce a 2D image of the cross-section ("slice"). If a 3D image is desired, the sample may be rotated on a stage 8 while successive 2D images are acquired. The 3D CT image is reconstructed when the rotation is completed. Alternatively, the x-ray source may be rotated around the sample to obtain a 3D image of the sample. Other mechanisms may be used to actuate relative rotation between the x-ray source and the sample to obtain x-ray attenuation data from a number of projection angles, as the aspects of the invention are not limited in this respect. It should be appreciated that some configuration will require the detector(s) to rotate in concert with the x-ray source to acquire the attenuation data.

Applicant has appreciated that it is beneficial to choose a material for the anode in the x-ray tube that will generate characteristic emission lines with energies that are larger than the energies of the monochromatic lines to be generated by the fluorescent target. This will improve the x-ray yield from the fluorescent target, but it is not a requirement on the embodiments of the invention. According to some embodiments wherein the field-of-view of the slit or pinhole may not encompass the entire sample, the sample may be translated in a direction perpendicular to the x-ray beam-detector line of site and the imaging procedure described in the foregoing repeated.

According to some embodiments, one or more x-ray lenses may be used to more efficiently collect the broad spectrum x-ray radiation emitted from the anode and focus the radiation onto a relatively small spot on the fluorescent target. For example, a glass capillary optic may be positioned between the anode and the fluorescent target to collect and focus the x-ray radiation. Use of one or more lenses may remove the need for a pinhole or other collimator between the fluorescent target and the sample. Since the optics will collect a larger amount of the x-rays emitted by the x-ray tube, the power of the x-ray tube may be reduced. The decrease in x-ray tube power may allow the apparatus to be air-cooled instead of water-cooled, further reducing the complexity and cost of the x-ray apparatus. It should be appreciated that one or more lens may be positioned between the fluorescent target and the sample to focus the monochromatic x-rays, either alone or in combination with optics arranged between the anode and the fluorescent target.

According to some embodiments, the X-ray apparatus in FIG. 9 is capable of generating pulsed monochromatic x-ray radiation. Pulsed x-ray radiation may be advantageous in reducing and/or eliminating motion artifacts in the resulting images due to motion of a human subject during radiation exposure. For example, imaging a beating heart using continuous x-ray radiation may cause blur in the resulting image(s) as the heart is in different locations/configurations at different times during the cardiac cycle. By pulsing the x-ray source, the x-ray radiation may be synced to the cardiac cycle such that imaging is performed at approximately the same time during the cardiac cycle to reduce and/or eliminate motion blur. It should be appreciated that any portion of the cardiac cycle may be imaged using such techniques. In addition, the breathing of a subject may result in similar motion artifacts and pulsing the x-ray source according to a predetermined exposure schedule may compensate for the motion caused by the subject's breathing (e.g., imaging may be performed during the approximate same time of the respiratory cycle). It should be appreciated that pulsing the radiation may be synced with other causes of subject motion, as the aspects of the invention are not limited in this respect.

According to some embodiments, x-ray pulsing is performed within the x-ray tube. For example, a timing circuit may be implemented to electronically open and close the circuit that generates the electrons flow from the cathode (e.g., filament) to the anode (target). This timing circuit may be configured to open and close the circuit according to any desired timing sequence. For example, the timing circuit may be controlled using a microcomputer having a clock to open and close the circuit according to a programmed timing sequence, which may be programmed to generate pulsed x-ray radiation according to any desired or any number of desired timing sequences.

According to some embodiments, x-ray pulsing is performed on the x-ray radiation itself. For example, a chopper (e.g., a rotating chopper) may be arranged to alternately block and pass either the broad spectrum radiation emitted from the first target and/or the monochromatic radiation emitted from the fluorescent target to achieve pulsed radiation according to a desired timing sequence. Dual choppers may be implemented to alternately block and pass both the broad spectrum radiation and the monochromatic radiation to achieve pulsed radiation at a desired timing sequence or at any number of desired timing sequences. It should be appreciated that other methods of generating pulsed x-ray radiation may be used, as the aspects of the invention are not limited in this respect. It should be appreciated that techniques for electronically pulsing the electron beam may be combined with techniques for blocking/passing the x-ray radiation, as the aspects of the invention are not limited for use with any type or combination of techniques for generating pulsed radiation.

Conventionally it was believed that monochromatic x-ray apparatus as described above would be incapable of generating satisfactory images and/or be unsuitable for performing radiation therapy. Applicant has appreciated and demonstrated the unexpected efficacy of using such apparatus for diagnostic and therapeutic purposes, as discussed in further detail below. According to some embodiments, x-ray apparatus as described herein are used to image a target tissue. According to some embodiments, the imaged tissue may be used to detect a biological anomaly (e.g., a tumor) and/or locate a biological anomaly for treatment. According to some embodiments, x-ray apparatus described herein are used at increased power levels to treat a located biological anomaly (e.g., destroy target tissue located during a prior imaging procedure). Examples of such techniques are described in further detail below.

Figure 10:
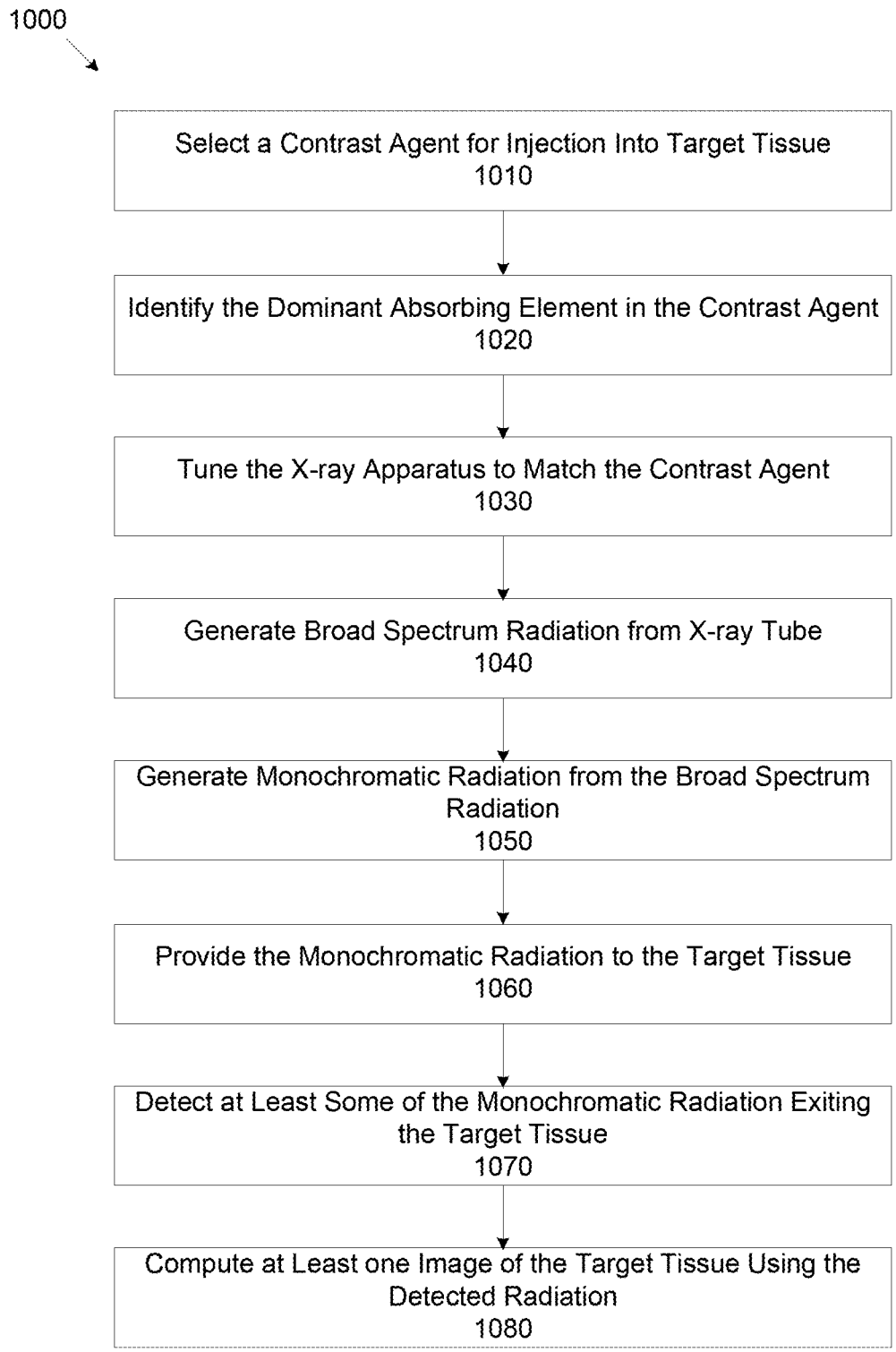
FIG. 10 is a flowchart illustrating a method of imaging using the monochromatic x-ray apparatus described above tuned to a selected contrast agent, in accordance with some embodiments of the present invention.

FIG. 10 is a flowchart illustrating a method using the monochromatic x-ray apparatus described above tuned to a selected contrast agent to image target tissue, in accordance with some embodiments of the present invention. Method 1000 may be used for imaging in 2D and 3D as desired. In act 1010, a contrast agent is chosen for injection into the subject tissue. The dominant element in the contrast agent may then be identified and a fluorescent target material chosen that will generate monochromatic x-rays with energies just higher than the absorption edge energy in the dominant element of the contrast agent (act 1020, 1030). While method 1000 is described in connection with contrast agents, it should be appreciated that the method may be performed without the use of contrast agents. In such circumstances, the fluorescent target may comprise material that generates monochromatic radiation at any suitable energy level.

The energy of characteristic x-rays emitted from a fluorescent target increase with atomic number. Therefore, when contrast agents are being used, the fluorescent target may be selected to comprise an element in the Periodic Table that will generate characteristic x-rays that exceed the absorption edge energy of the contrast agent. For example, when the dominant element in a given contrast agent is iodine (which has an atomic number of 53), the energy of the K absorption edge of iodine is 33.24 keV. The next element in the Periodic Table with characteristic x-ray energies greater than 33.24 keV is Lanthanum, with atomic number 57. The Lanthanum K x-ray has an energy of 33.4 keV which is 0.16 keV above the iodine absorption edge. While it may be beneficial to select the next element in the Periodic Table that will produce x-rays having energy that exceeds the absorption edge of the dominant element in the contrast agent, such an element may not be practical for every contrast agent. Accordingly, when contrast agents are used, any element that produces x-rays exceeding the absorption edge of the contrast agent may be used, as the aspects of the invention are not limited in this respect.

A conventional x-ray tube that produces broad spectrum radiation may be used to irradiate the fluorescent target (act 1040). For example, the high voltage between the cathode and anode in the x-ray tube may be adjusted to a value that will produce broad spectrum radiation with energies that are at least 3-5 times the energy of the desired fluorescent x-rays. In some embodiments, the broad spectrum radiation will include characteristic line emission from the anode material in addition to the Bremsstralung radiation. Monochromatic x-rays are generated from the fluorescent target in response to incident broad spectrum radiation (act 1050). The monochromatic x-rays may be directed to irradiate the target tissue (act 1060). Since the size of the spot on the fluorescent target is usually a few millimeters in diameter, a pinhole may be used to establish a source of x-rays originating from a smaller diameter spot to improve spatial resolution in the image. The point source of x-rays diverges in the shape of a cone. These x-rays pass through the sample tissue and are detected by a 2D imaging x-ray detector (1070).

The attenuation data acquired by the detectors may then be used to reconstruct a 2D image of the target tissue (act 1080). If a 3D CT scan is desired, successive 2D images may be acquired at different projection or view angles about the target tissue, using any of the techniques described in the foregoing (e.g., acts 1040-1080 may be repeated at different angles around an axis that is perpendicular to the line of site between the x-ray emission and the detector). It should be appreciated that method 1000 may be performed using either continuous x-ray generation or pulsed x-ray generation according to any desired timing sequence.

According to some embodiments, a slit (or any other collimator) may be substituted for the pinhole. The resulting x-ray emission will take the form of a narrow fan beam. The tissue may be rotated around the axis perpendicular to the x-ray beam-detector line-of-site to produce a 3D CT image. The tissue sample may then be translated along the said perpendicular axis to obtain another 3D CT image of adjacent tissue.

According to some embodiments, a contrast agent may not be necessary. Since monochromatic x-rays produce higher image contrast than broad band x-rays, it may suffice to choose a fluorescent target that will generate x-rays with energies that will preferentially be absorbed in denser tissue.

Figure 11:
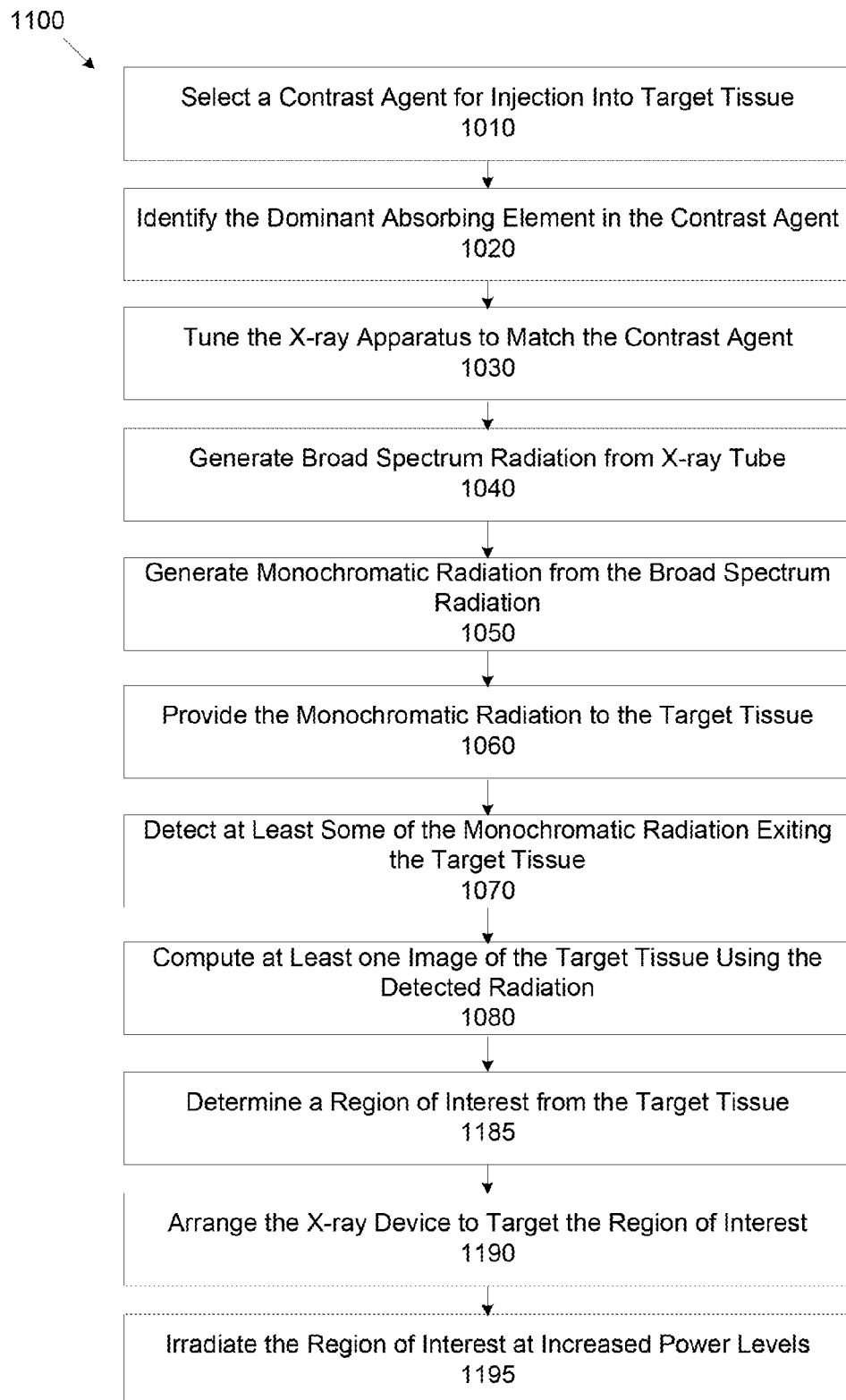
FIG. 11 is a flowchart illustrating a method of radiation therapy using the monochromatic x-ray apparatus described above, in accordance with some embodiments of the present invention

FIG. 11 is a flowchart illustrating a method of radiation therapy using the monochromatic x-ray apparatus described above, in accordance with some embodiments of the present invention. Method 1100 may be used, for example, to treat cancerous tumors (e.g., by irradiating malignant tissue to destroy the tumor). Initially, the method described in connection with FIG. 10 may be performed, which produces a 2D or 3D x-ray image of the target tissue (e.g., acts 1010-1080 may be performed and acts 1040-1080 may be repeated as desired). This procedure may be performed with the x-ray tube operating at a relatively low power suitable for imaging. It may be performed immediately before the therapy is to begin, or it may be performed as a repeat procedure to verify the location of the tumor which was discovered during prior diagnostic imaging.

Once the target tissue is imaged, a region of interest is located (e.g., a tumor is located via the imaging procedure) (act 1185). The x-ray device may be arranged to target the region of interest (act 1190) and the power of the x-ray tube increased beyond the relatively low levels needed for imaging and the region of interest irradiated (1195). The absorption of high energy monochromatic x-rays is enhanced by the contrast agent localized in the tumor. For example, if the contrast agent includes gold, the K shell ionization energies are approximately 80 keV. The attenuation lengths for these photons are about 20 cm so the K x-rays will serve not only as a diagnostic, but it will enhance the treatment in as much as the K radiation excites the atoms in the contrast agent in the tumor. The resultant L shell fluorescent emission that takes place as the high Z atom de-excites, has a short attenuation length—about 1 cm, so these L x-rays (9.7 keV in Au) will serve to destroy the tissue. Depending on the size of the tumor, a larger pinhole may be required to encompass the tumor, or it may be necessary to translate or rotate the tissue (or the x-ray source) to fully destroy the tumor.

Accordingly, various aspects of the invention allow for a relatively low cost, relatively small footprint x-ray apparatus for generating monochromatic radiation suitable for imaging and/or radiation therapy. Such an apparatus is presently unavailable for clinical/medical x-ray diagnostic/therapeutic applications. Medical facilities such as clinics and hospitals are presently performing such diagnostic/therapeutic applications using x-ray apparatus that emit broad spectrum radiation, which has many shortcomings with respect to image quality, patient radiation dose, collateral tissue damage, etc.

Figure 12:
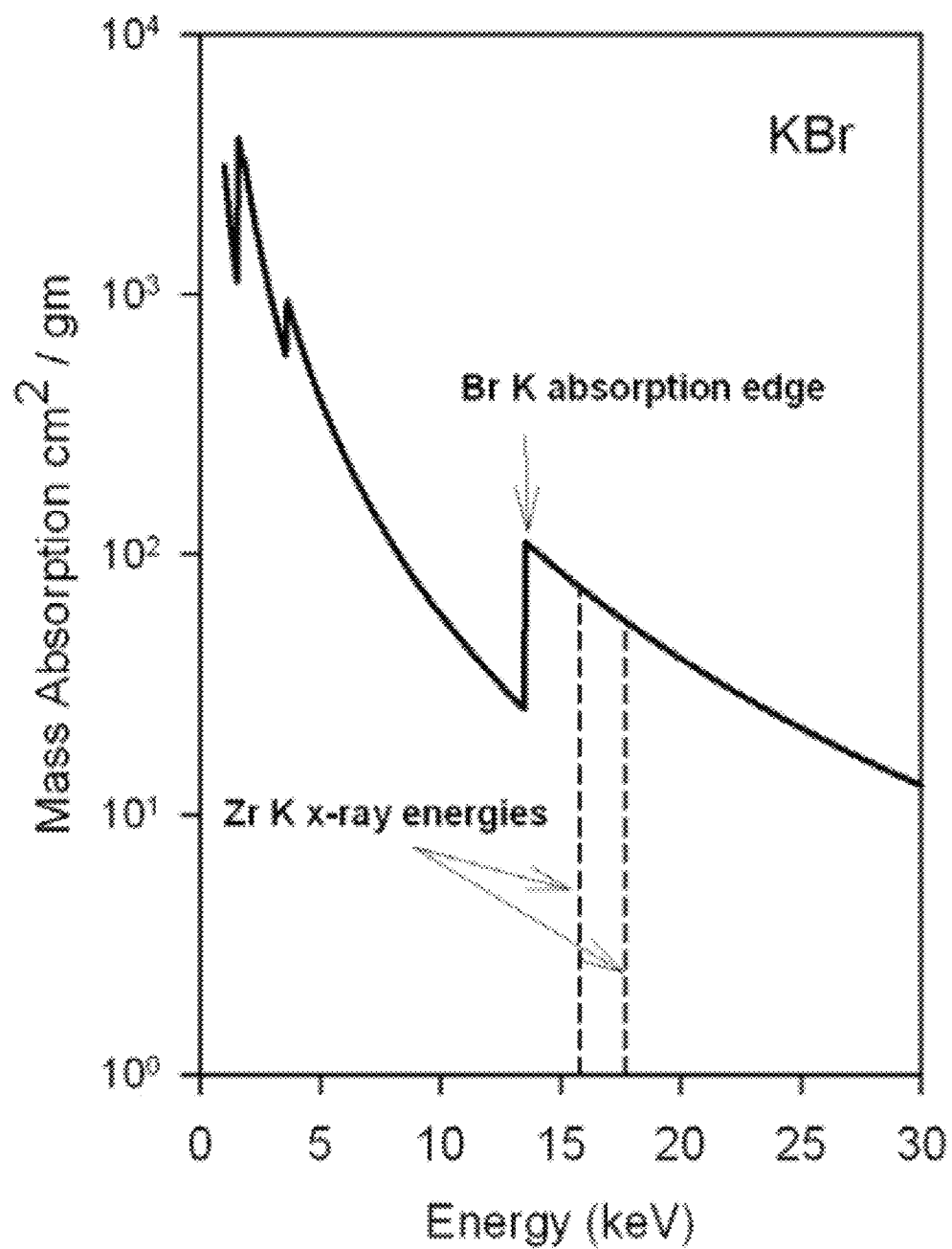
FIG. 12 illustrates the mass absorption coefficient for potassium bromide (KBr)

According to some embodiments, a conventional, tabletop, x-ray tube is used to irradiate a thick target of zirconium (Zr). Zr will emit fluorescent K$\alpha$ and K$\beta$ x-rays at 15.77 keV and 17.67 keV, respectively. These X-rays pass through a 0.5 mm diameter pinhole and then through a subject sample. A 2D image is made with an x-ray detector. The sample can be rotated around an axis orthogonal to the divergent beam. This enables a CT image to be obtained (not shown). The sample used in this demonstration was a phantom, i.e., a composite material fabricated to simulate living tissue. It contained localized concentrations of potassium bromide (KBr) to mimic the contrast agent in live tissue. Bromine, in the form of bromodeoxyuridine (BudR), is a relevent choice for this demonstration; it is commonly used as a contrast agent because it localizes in tumor cells. The energies of the monochromatic Zr X-rays are just above the energy of the bromine absorption edge and will consequently be absorbed with higher efficiency than the surrounding material (e.g., In FIG. 12, the vertical dotted lines are located at the energies of the Zr K$\alpha$ and K$\beta$ x-ray lines, respectively. Their energies are just above the K absorption edge in the bromine. The intensity of the K$\alpha$ line dominates).

Figures 13A, 13B:
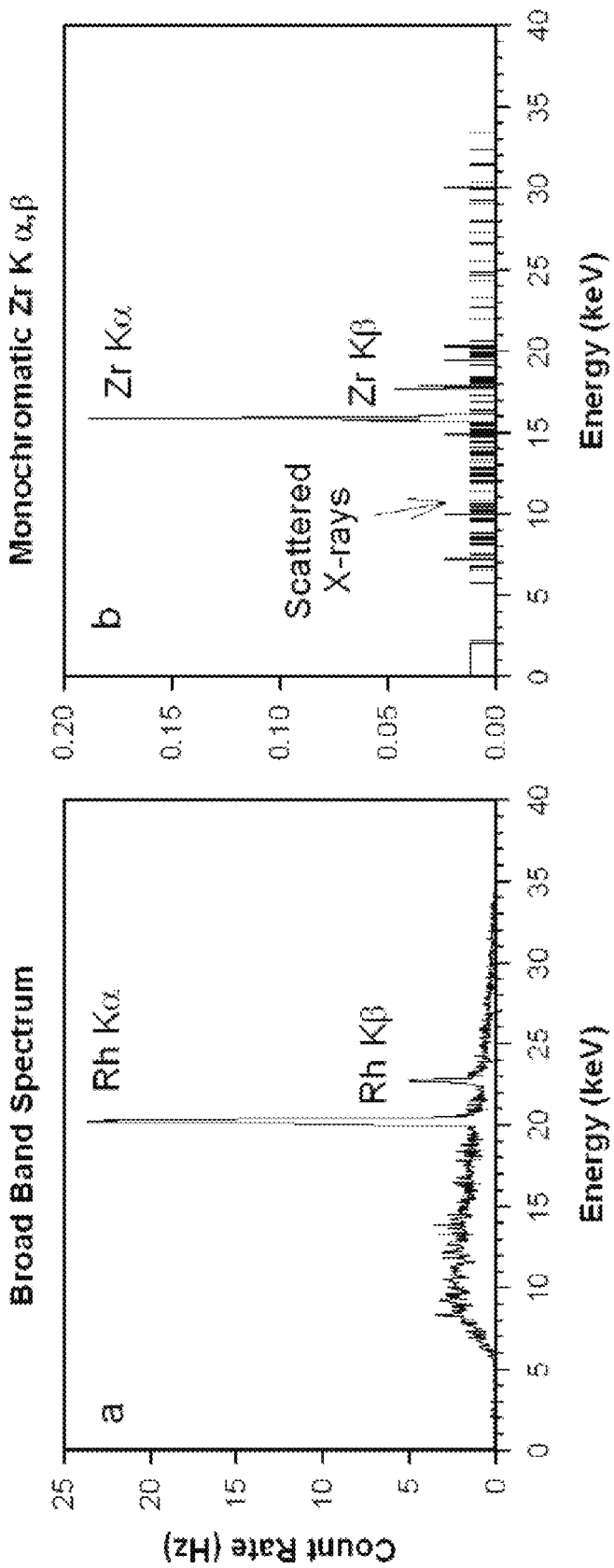
FIGS. 13A and 13B illustrate the thick target Bremsstrahlung spectrum generated by the conventional x-ray tube with a rhodium anode and the Zr Kα and Kβ x-rays produced by x-ray fluorescence using the broad band spectrum in FIG. 13A, respectively.

The conventional x-ray tube generates a thick target broad band Bremsstrahlung spectrum as shown in FIG. 13*a*. The x-ray tube has a rhodium anode and the two peaks in the spectrum are rhodium K$\alpha$ and K$\beta$ line emission resulting from the electron excitation in the x-ray tube. The spectrum in FIG. 13*b* shows the monochromatic Zr K$\alpha$ and K$\beta$ X-rays that are produced via fluorescence when the X-rays in the broad spectrum radiation irradiate the Zr target. The imaging quality and total absorbed dose for an x-ray image made with the broad spectrum radiation is compared with an image made with the monochromatic spectrum. It should be appreciated that the lines denoted by scattered x-rays are an artifact of the detectors and not an indication that the radiation from the fluorescent target is polychromatic, which is monochromatic.

Figures 14A, 14B:
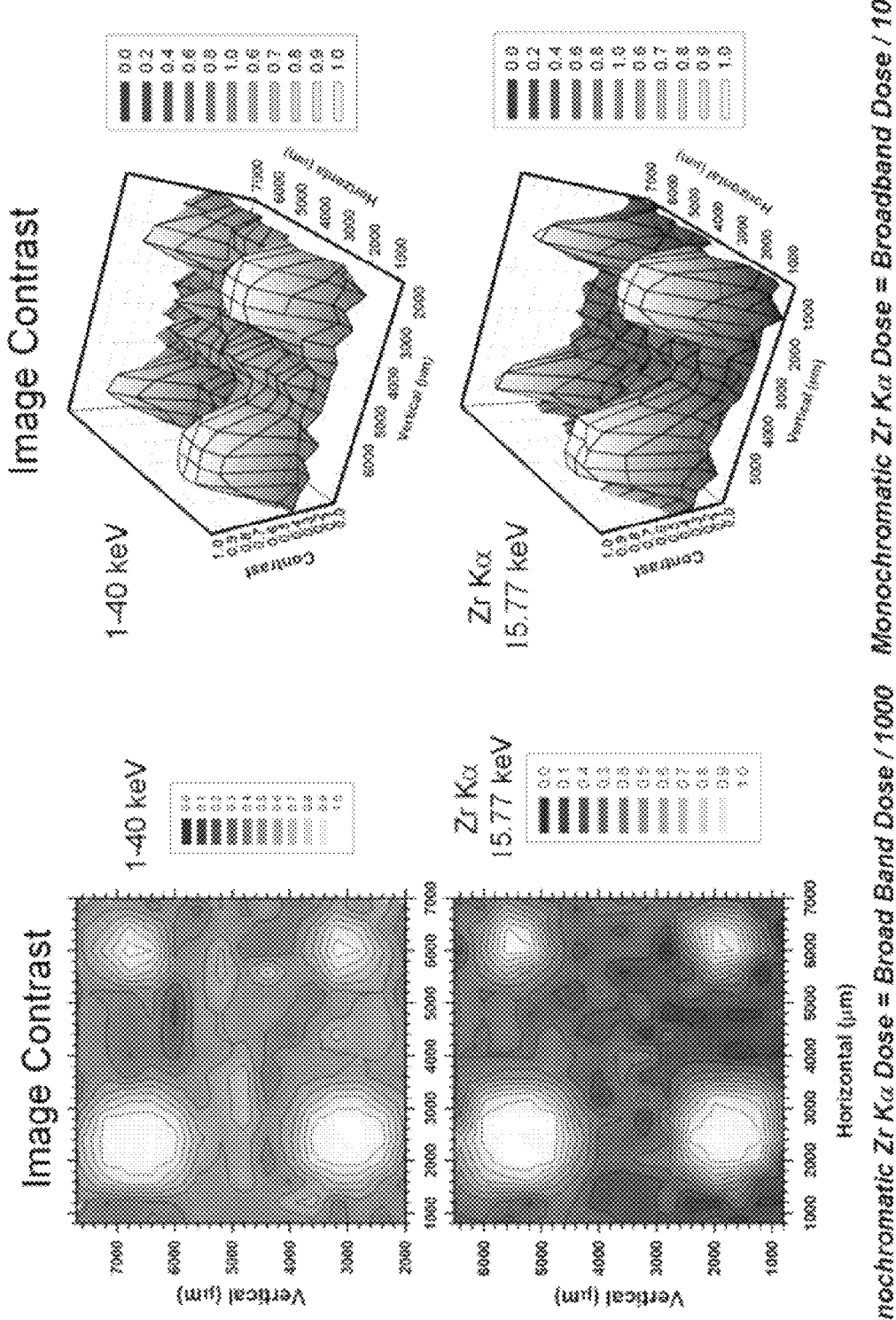
FIG. 14A illustrates a 2-D contour plot of the KBr phantom using the Bremsstrahlung spectrum (top) and a 2-D contour of the KBr phantom using monochromatic Zr K x-rays in accordance with embodiments of the invention, respectively.
FIG. 14B illustrates a 3-D plot of the x-ray intensity of the KBr phantom using the Bremsstrahlung spectrum (top) and a 3-D plot of x-ray intensity of the KBr phantom using the monochromatic Zr K x-rays according to some embodiments of the invention, respectively.

These results are shown in FIGS. 14A and 14B. The 2-D contour plot of the x-ray intensity at the top of FIG. 14A and the 3-D plot of the x-ray intensity at the top of FIG. 14B were made with the broad band spectrum. To achieve this, the Zr target was removed from the beam line and the pinhole, sample and x-ray detector combination were positioned directly in the line of site to the x-ray tube. These components were returned to their original position for the monochromatic x-ray measurement. The 2-D contour plot of the x-ray intensity and 3-D plot of the x-ray intensity made with the monochromatic radiation are depicted at the bottom of FIGS. 14A and 14B, respectively. The figures clearly demonstrate that the contrast is better in the monochromatic images. Furthermore, the absorbed dose to the sample is 1000 times less using the monochromatic radiation.

Combined with recent advances in nano-biotechnology, the implications of this table-top fluorescent technique are far reaching because it simply and efficiently uses x-ray radiation that is as monochromatic as atomic physics allows. For early detection, this diagnostic imaging technique can achieve higher sensitivity and higher specificity at lower body dose than conventional methods. For therapy, the dose to normal tissue will also be significantly reduced. All this at a low cost and in a package that can fit in a typical doctor's office or laboratory.

The above-described embodiments of the present invention can be implemented in any of numerous ways, and the examples described herein are not limiting. In addition, various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

What is claimed is:

1. A method comprising:
generating broad spectrum x-ray radiation from an x-ray tube comprising a first target that, in response to being irradiated by electrons, emits the broad spectrum x-ray radiation;
directing at least some of the broad spectrum x-ray radiation to irradiate a second target comprising material that, in response to the irradiation, emits monochromatic x-ray radiation;
directing at least some of the monochromatic x-ray radiation to irradiate subject matter of interest from a plurality of angles about the subject matter of interest;
detecting at least some of the monochromatic x-ray radiation transmitted through the subject matter of interest from the plurality of angles; and
generating at least one 3D image based, at least in part, on the detected monochromatic x-ray radiation.

2. The method of claim 1, wherein the second target absorbs at least some of the broad spectrum x-ray radiation and in response emits the monochromatic x-ray radiation via fluorescence.

3. The method of claim 1, wherein the monochromatic x-ray radiation is emitted above an absorption edge of the subject matter of interest, wherein the absorption edge is at a binding energy of one of a K-shell, an L-shell or a M-shell electron of the subject matter of interest.

4. The method of claim 1, wherein the subject matter of interest includes tissue, the method further comprising increasing a power level of the x-ray tube and directing the monochromatic x-ray radiation such that it irradiates locations within the tissue corresponding to a region of interest.

5. The method of claim 1, wherein the power level of the x-ray tube is increased by an amount sufficient to destroy at least some of the tissue.

6. The method of claim 1, wherein the x-ray tube is a table-top sized component.

7. The method of claim 1, wherein directing at least some of the monochromatic x-ray radiation to irradiate the subject matter of interest comprises directing at least some of the monochromatic x-ray radiation to irradiate subject matter of interest via a single aperture.

8. The method of claim 7, wherein the single aperture reduces a spot-size of the monochromatic x-ray radiation directed to irradiate the subject matter of interest to improve the spatial resolution of the at least one image.

9. The method of claim 1, wherein the second target includes a first fluorescent target and a second fluorescent target, the method comprising:
directing at least some broad spectrum x-ray radiation to irradiate the first fluorescent target that, in response to the irradiation, emits first monochromatic x-ray radiation at an energy above an absorption edge of the subject matter of interest; and
directing at least some broad spectrum x-ray radiation to irradiate the second fluorescent target that, in response to the irradiation, emits second monochromatic x-ray radiation at an energy below an absorption edge of the subject matter of interest;
directing at least some of the first monochromatic x-ray radiation and at least some of the second monochromatic x-ray radiation to irradiate the subject matter of interest at the plurality of angles;
detecting at least some of the first monochromatic x-ray radiation and at least some of the second monochromatic x-ray radiation at the plurality of angles; and
generating at least one 3D image based, at least in part, on a difference between the detected first monochromatic x-ray radiation and the detected second monochromatic x-ray radiation.

10. An x-ray apparatus comprising:
an electron source configured to generate electrons;
at least one first target arranged to receive electrons from the electron source, the at least one first target comprising material that, in response to being irradiated by the electrons, emits broad spectrum x-ray radiation;
at least one second target arranged to receive at least some of the broad spectrum x-ray radiation, the at least one second target comprising material that, in response to irradiation by broad spectrum x-ray radiation from the first target, emits monochromatic x-ray radiation to irradiate subject matter of interest from a plurality of angles about the subject matter of interest; and
at least one detector positioned to detect at least some of the monochromatic x-ray radiation emitted from the at least one second target and transmitted through the subject matter of interest from the plurality of angles to form, at least in part, at least one 3D image of at least a portion of the subject matter of interest.

11. The x-ray apparatus of claim 10, wherein the at least one second target absorbs at least some of the broad spectrum x-ray radiation and in response emits the monochromatic x-ray radiation via fluorescence.

12. The x-ray apparatus of claim 10, wherein the at least one second target includes a plurality of second targets, each of the plurality of second targets comprising material that, in response to irradiation by broad spectrum radiation, emits monochromatic x-ray radiation at a different energy.

13. The x-ray apparatus of claim 10, wherein the at least one second target includes a first fluorescent target and a second fluorescent target, the first fluorescent target comprising material that, in response to irradiation by broad spectrum radiation, emits monochromatic x-ray radiation at an energy level above an absorption edge associated with first subject matter of interest, and the second fluorescent target comprising material that, in response to irradiation by broad spectrum radiation, emits monochromatic x-ray radiation at an energy level above an absorption edge associated with second subject matter of interest.

14. The x-ray apparatus of claim 10, wherein the electron source and the at least one first target are housed in an x-ray tube that has a table-top sized footprint.

15. The x-ray apparatus of claim 10, further comprising at least one optical component arranged between the at least one first target and the at least one second target to collect and focus the broad spectrum x-ray radiation on the at least one second target and/or at least one optical component arranged between the at least one second target and the subject matter of interest to collect and focus the monochromatic x-ray radiation.

16. The x-ray apparatus of claim 10, further comprising a power control configured to vary power levels of the x-ray apparatus depending on whether the x-ray apparatus is being used for imaging or radiation therapy.

17. The x-ray apparatus of claim 10, further comprising a single aperture arranged such that at least some monochromatic x-ray radiation, when emitted from the at least one second target, passes through the single aperture to irradiate the subject matter of interest.

18. The x-ray apparatus of claim 17, wherein the single aperture reduces a spot-size of the monochromatic x-ray radiation that, when emitted, irradiates the subject matter of interest to improve the spatial resolution of the at least one image.

19. The x-ray apparatus of claim 18, wherein the single aperture is approximately 0.5 mm in diameter to reduce the spot-size of the monochromatic x-ray radiation that, when emitted, irradiates the subject matter of interest.

20. The x-ray apparatus of claim 12, wherein at least one of the plurality of second targets, in response to being irradiated by broadband radiation, emits monochromatic x-ray radiation at an energy level above an absorption edge associated with the subject matter of interest and at least one of the plurality of second targets, in response to being irradiated by broadband radiation, emits monochromatic x-ray radiation at an energy level below an absorption edge associated with the subject matter of interest.

* * * * *